US00PP28784P2

(12) United States Plant Patent
Hansen

(10) Patent No.: US PP28,784 P2
(45) Date of Patent: Dec. 19, 2017

(54) ***HOSTA* PLANT NAMED 'BEYOND GLORY'**

(50) Latin Name: ***Hosta* hybrid (Tratt.)**
Varietal Denomination: Beyond Glory

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 14/999,732

(22) Filed: Jun. 21, 2016

(51) Int. Cl.
*A01H 5/02* (2006.01)

(52) U.S. Cl.
USPC ..... Plt./353

(58) Field of Classification Search
USPC ..... Plt./353

CPC ..... A01H 5/0272; A01H 5/02; A01H 5/12; A01H 5/22; A01H 5/00
See application file for complete search history.

(56) References Cited

PUBLICATIONS

American *Hosta* Society Online Auction Results p. 2015 retrieved on Jul. 24, 2017, retrieved from the Internet at <http://www.americanhostasociety.org/Activities/ahsresults15.htm> pp. 1-4.*
Cox's Plant Farm 2016 Spring Catalog retrieved on Jul. 20, 2017, retrieved from the Internet at <file:///a/Users/jhwu/Downloads/Cox's%20Plant%20Farm%20-%202016-Catalog.pdf> pp. 1, 6-7.*

* cited by examiner

*Primary Examiner* — June Hwu

(57) ABSTRACT

A new and distinct *Hosta* plant named 'Beyond Glory' with foliage having stiff, thick-substance cordate blades of very wide dark green margins, and with leaf centers of yellow to chartreuse. The light-lavender flowers are very tightly congested on vertical scapes well above foliage in mid to late summer.

2 Drawing Sheets

Latin botanical classification: *Hosta* hybrid (Tratt.).
Variety denomination: 'Beyond Glory'.

BACKGROUND AND ORIGIN OF THE PLANT

The present invention relates to a new and distinct *hosta* plant, *Hosta* 'Beyond Glory' hereinafter also referred to as the new plant or just the cultivar name, 'Beyond Glory'. *Hosta* 'Beyond Glory' was discovered by the inventor as a non-induced, naturally-occurring, whole-plant mutation in a batch of tissue cultured propagated *Hosta* 'Old Glory' U.S. Plant Pat. No. 12,503 in a greenhouse at a wholesale perennial nursery in Zeeland, Mich., USA in spring of 2010. The new plant has been asexually propagated by division at the same nursery in Zeeland, Mich., USA since 2014 and also by careful shoot tip plant tissue culture with the resultant asexually propagated plants having retained all the same traits as the original plant. 'Beyond Glory' is stable and reproduces true to type in successive generations of asexual reproduction.

No plants of *Hosta* 'Beyond Glory' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

*Hosta* 'Beyond Glory' was first asexually propagated from a single select plant in 2013 by careful, sterile, shoot-tip tissue culture at the same nursery in Zeeland, Mich. The resultant asexually propagated plants have been found to be stable and true to type in successive generations of asexual reproduction.

BRIEF SUMMARY OF THE PLANT

There are over 5,600 registered *hosta* cultivars with The American *Hosta* Society, which is the International Cultivar Registration Authority for the genus *Hosta* and a similar number of unregistered cultivars.

The nearest comparison variety is sport parent *Hosta* 'Old Glory' U.S. Plant Pat. No. 12,503, and the new plant differs from 'Old Glory' by having wider variegated margins, thicker substance to the foliage and slightly darker green leaf centers.

Other similar *Hosta* cultivars known to the inventor include: 'Beckoning' U.S. Plant Pat. No. 18,371, 'June Spirit' U.S. Plant Pat. No. 25,593, 'Olive Branch' (not patented), 'Orange Marmalade' U.S. Plant Pat. No. 16,742, 'Paul's Glory' (not patented), and 'Princess Anastasia' (not patented).

The leaves of the new plant are more rounded than 'Beckoning', 'June Spirit', 'Olive Branch', 'Orange Marmalade', 'Paul's Glory' and 'Princess Anastasia', larger than 'June Spirit' and 'Olive Branch', and brighter yellow in center than 'Beckoning' and 'Olive Branch'. The flowers of 'Beyond Glory' are also closer together on the individual panicles than each of the above comparison plants and are slightly different colored. The leaf blades of 'Beckoning', 'Paul's Glory' and 'Princess Anastasia' are more rugose and glaucous adaxial.

Other *Hosta* cultivars have similar variegation colors or pattern, or other individual traits similar to 'Beyond Glory', but among the characteristics in combination which distinguish the new plant from the above cultivars and all other *hostas* known to the applicant are:

1. Dense rounded plant habit and leaves with stiff thick substance;
2. Cordate-shaped variegated foliage with very broad, dark green margins and narrow centers of yellow to chartreuse;
3. Medium lavender flowers held tightly together well above foliage, each flower subtended by broad bract;
4. Stiff, vertical, chartreuse scapes.
5. Early scape with young flower buds completely encapsulated by series of many bracts.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
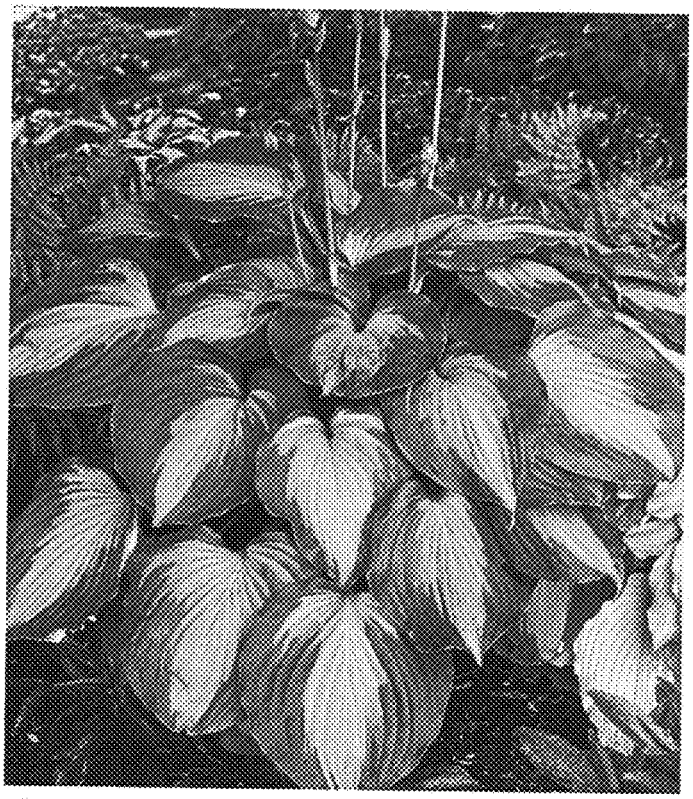
FIG. 1 shows a three-year old *Hosta* 'Beyond Glory' plant in a shaded garden at a nursery in Zeeland, Mich. with supplement fertilizer and water as needed.
Figure 2:
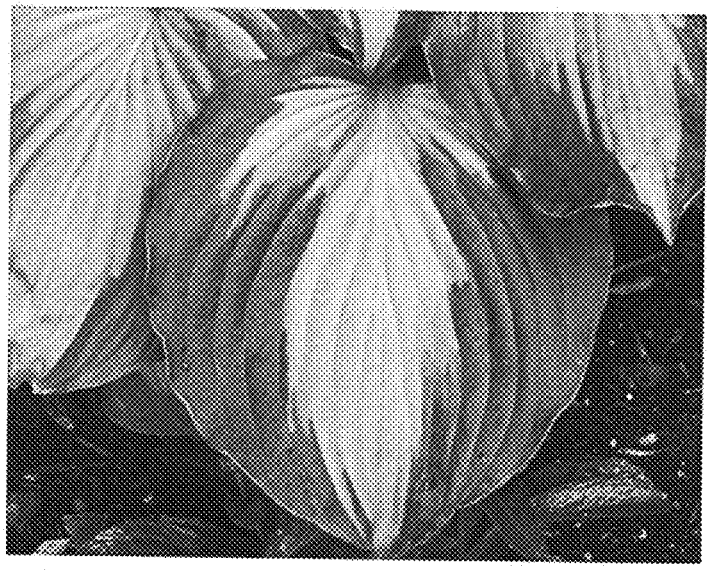
FIG. 2 shows a close-up of a leaf before flowering showing very wide variegated margins.
Figure 3:
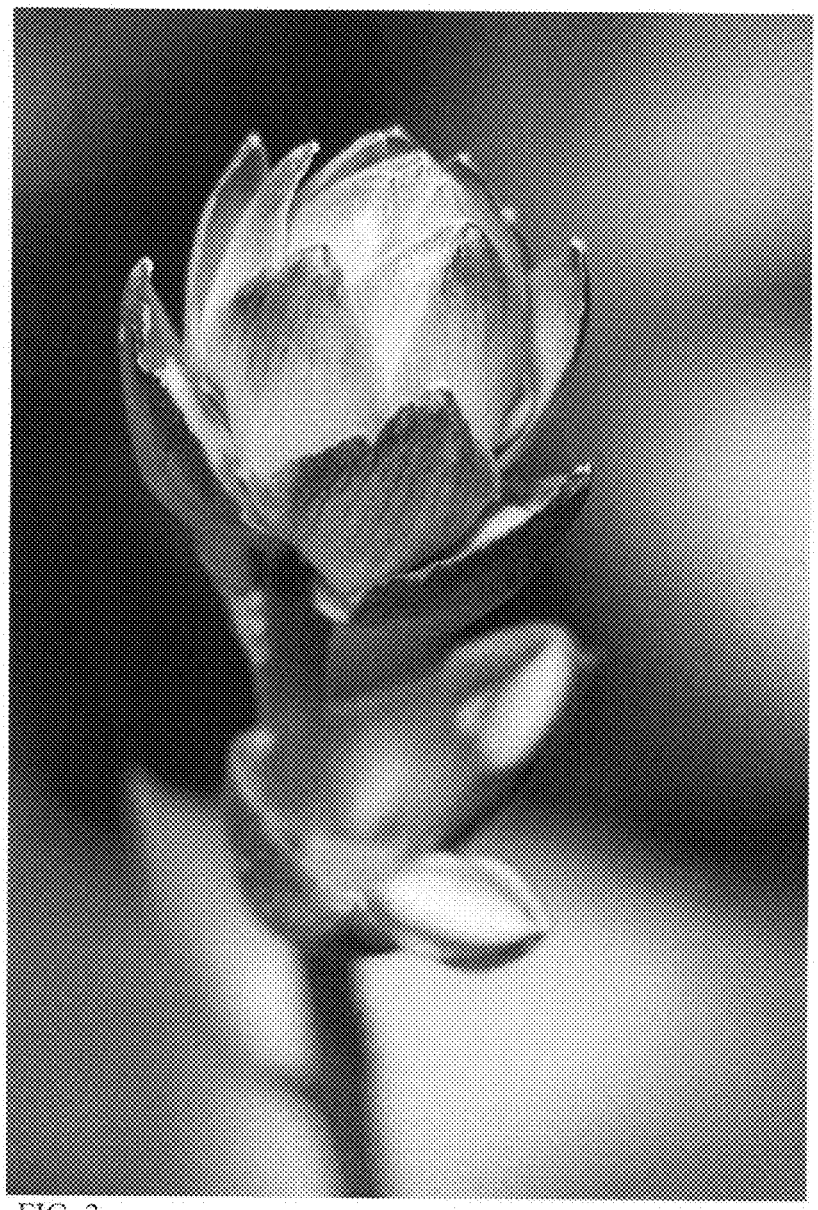
FIG. 3 shows a close-up of the scape and buds of 'Beyond Glory'.

The following descriptions and color references are based on the 2001 edition of The Royal Horticultural Society Colour Chart except where common dictionary terms are used. The new plant, *Hosta* 'Beyond Glory', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with supplemental water and fertilizer. One skilled in the art would also recognize that the phenotype would vary with maturity as the plant ages without being divided.

Botanical classification: *Hosta* hybrid.

Parentage: Whole-plant mutation of *Hosta* 'Old Glory' U.S. Plant Pat. No. 12,503.

Propagation: Garden division and sterile plant tissue culture.

Time to initiate roots from tissue culture: About two to three weeks.

Growth rate: Rapid.

Crop time: Under normal winter and spring growing conditions about 16 to 20 weeks to finish from a from rooted tissue culture liner to a 65 mm pot.

Rooting habit: Normal, fleshy, lightly branching.

Plant shape and habit: Hardy herbaceous perennial with basal rosette of leaves emerging from rhizomes producing a short symmetrical mound of broadly horizontal leaves.

Plant size: Foliage height about 40.0 cm above soil line to the top of the leaves and about 94.0 cm wide at the widest point slightly above the soil line.

Foliage description: Margin entire, slightly repand; glabrous, slightly glaucous adaxial, highly glaucous abaxial; cordate, acuminate to cuspidate leaf apex with cordate base; apex deflexed in about terminal 2.0 cm.

Leaf blade: About 22.5 cm long and about 21.5 cm wide; variegated with dark green margin to about 8.4 cm across and average about 4.0 cm across, and chartreuse to yellow center to as narrow as about 4.5 cm across and average about 8.0 cm wide.

Leaf blade color: Early season shortly after emergence adaxial (top) center color nearest RHS 144A; early season adaxial margin between RHS 138A and RHS 146A; early season abaxial (underside) center nearest RHS 137C; early season abaxial margin between RHS 138A and RHS 138B; just prior to flowering adaxial center nearest RHS N144A, adaxial margin nearest RHS 137A; just prior to flowering abaxial center nearest RHS 138B, abaxial margin nearest RHS 137B; the region between the margin and center typically shows a gradual melding or infusing of the two leaf colors for the intermediate 1.0 to 2.0 cm; mid-season and later summer adaxial centers between RHS 145A and RHS 145C; mid-season and later adaxial margins between RHS 137A and RHS 139A; mid-season and later abaxial center blend between RHS 138C and RHS 144C; mid-season and later abaxial margins between RHS N138B and RHS 138C; intermediate colors where adaxial and abaxial leaf blade margins and centers unevenly and irregularly fold over each other typically comprising a melding of the leaf center and leaf margin colors with some distinct feathering jetting from the margin into the center of lighter than RHS 146D.

Petiole: Entire, glabrous, concavo-convex; abaxial glaucous, adaxial slightly glaucous; mostly straight from base of plant to leaf base with little bending or curving, stiff, attitude upward to outward; to about 30.0 cm long and to about 15.0 mm wide at base, average about 28.0 cm long and 12.0 mm wide; variegated margin width about 1.0 mm wide.

Petiole color: Adaxial center nearest RHS 145A, and adaxial margin nearest RHS 137A; abaxial center nearest RHS 147D and abaxial margin nearest RHS 146B.

Veins: Parallel, campylodrome; raised on abaxial side, typically about 13 to 14 vein pairs plus midrib.

Veins color: Adaxial and abaxial veins the same color as the surrounding tissue.

Flower description:

Buds one day prior to opening: Globose with rounded apex and narrow base; about 1.5 cm in diameter with base narrowing at about mid-length to about 0.4 cm diameter; about 4.8 cm long; Bud color: nearest RHS 84D.

Flowers: Perfect; funnelform; held outright to slightly upright; about 5.5 cm long and 3.8 cm wide, fused portion about 2.8 cm long and 4.0 mm diameter, distal flowers progressively slightly smaller; persists for a normal period, usually one day on plant or as cut flower; flowers effective from early summer for about three weeks with about 30 to 40 flowers per scape; attitude outward to slightly upward.

Flower fragrance: None detected.

Tepal: Two sets of three; glabrous; margins entire; fused at base; with acute apex; inner set approximately 5.5 cm long and 2.0 cm wide; outer set approximately 5.5 cm long and 2.1 cm wide.

Tepal color: Coloring of both sets similar with inner set having about a 1.0 mm wide darker margin of nearest RHS 83D; adaxial and abaxial centers between RHS N82D and RHS N81D with adaxial and abaxial basal margins lighter than RHS 84D; abaxial corolla tube base lighter than RHS 84D and distally between RHS N82D and BBS N81D.

Tepal veins: Indistinguishable in color and form from surrounding tissue.

Gynoecium: Single; tri-carpelled.

*Style*.—Single, approximately 6.6 cm long, 1.5 mm diameter, curved upward in distal 1.0 cm about 90 degrees; color lighter than RHS 155D.

*Stigma*.—Globose, about 2 mm in diameter; color nearest RHS 155D.

*Ovary*.—Ovoid, about 7.0 mm long and 3.0 mm diameter at widest; color nearest RHS 145B.

Androecium:

*Filaments*.—Six, approximately 6.1 cm long and 1.0 mm in diameter; curved upward to nearly 90 degrees in the apical 1.0 cm; color nearest RHS 155D.

*Anthers*.—Elliptic; dorsifixed, versatile, longitudinal; about 4.0 mm long and 1.5 mm wide; color nearest RHS N187A.

*Pollen*.—Elliptic, less than 0.1 mm long, color nearest 11B.

Peduncle: Usually one per mature division; glaucous, glabrous; attitude upright; up to about 74.0 cm tall, and up to 10.0 mm diameter at base, average about 68.0 cm long and 9.0 mm diameter.

Peduncle color: Nearest RHS 146C.

Pedicel: Short, glabrous; slightly curved; attitude outright to slightly upright; approximately 8.0 mm long and 2.5 mm diameter.

Pedicel color: Nearest RHS 146C with slight tinting of nearest RHS N187B.

Scape bracts: Ovate; glaucous; glabrous; entire margin, sessile partially clasping base; concavo-convex; each flower normally subtended by a single bract with typically two to three bracts below first flower; average lowest bract about 4.5 cm long and 2.3 cm wide at middle decreasing distally.

Scape bract color: At time of flowering abaxial apical one-third to one-half nearest RHS N186C, abaxial base nearest RHS 145D; adaxial nearest RHS 145D.

Fruit: Non-fleshy, dehiscent, tri-loculicidal capsule; oblong ellipsoidal; about 2.9 cm long and 6.0 mm diameter; color as maturing nearest RHS 137B and when mature nearest RHS 164C.

Seed: Elliptic with flattened wing surrounding embryo situation toward one end of ellipse; about 10 mm long, 4.0 mm wide at middle and 1.0 mm thick at embryo; typically few per capsule, about 4 to 8; color nearest RHS 202A with maturity.

Disease tolerance and resistance: The new plant has not shown any resistance to pests and diseases common to *hostas*. *Hosta* 'Beyond Glory' grows best and shows best coloration with plenty of moisture, adequate drainage and light shade, but is able to tolerate some drought when mature. Hardiness at least from USDA zone 3 through 9, and other disease resistance is typical of that of other *hostas*.

I claim:

1. A new and distinct ornamental plant cultivar named *Hosta* 'Beyond Glory' as herein described and illustrated.

* * * * *